US012605250B2

(12) United States Patent
Ginn et al.

(10) Patent No.: US 12,605,250 B2
(45) Date of Patent: Apr. 21, 2026

(54) SYSTEMS APPARATUS AND METHODS FOR STABILIZING SACROILIAC JOINTS

(71) Applicant: Tenon Medical, Inc., Los Gatos, CA (US)

(72) Inventors: Richard S Ginn, Powhatan, VA (US); Richard Brown, Colorado Springs, CO (US)

(73) Assignee: Tenon Medical, Inc., Los Gatos, CA (US)

( * ) Notice: Subject to any disclaimer, the term of this patent is extended or adjusted under 35 U.S.C. 154(b) by 0 days.

(21) Appl. No.: 19/083,696

(22) Filed: Mar. 19, 2025

(65) Prior Publication Data

US 2025/0302632 A1    Oct. 2, 2025

Related U.S. Application Data

(60) Provisional application No. 63/569,906, filed on Mar. 26, 2024.

(51) Int. Cl.
*A61F 2/30* (2006.01)

(52) U.S. Cl.
CPC    *A61F 2/30988* (2013.01); *A61F 2002/30995* (2013.01)

(58) Field of Classification Search
CPC ........ A61F 2002/30995; A61F 2/30988; A61F 2/4455; A61F 2/447
See application file for complete search history.

(56) References Cited

U.S. PATENT DOCUMENTS

| | | | | |
|---|---|---|---|---|
| 6,371,987 B1 * | 4/2002 | Weiland | ................ | A61F 2/4455 |
| | | | | 623/17.11 |
| 6,743,256 B2 * | 6/2004 | Mason | .................... | A61F 2/447 |
| | | | | 623/17.11 |
| 7,837,732 B2 * | 11/2010 | Zucherman | ............. | A61F 2/446 |
| | | | | 623/17.11 |
| 8,617,244 B2 * | 12/2013 | Reichen | ................ | A61F 2/4455 |
| | | | | 623/17.11 |
| 11,337,821 B2 * | 5/2022 | Mauldin | ................ | A61B 17/16 |
| 11,752,011 B2 * | 9/2023 | Stuart | .................... | A61F 2/447 |
| | | | | 623/17.11 |
| 12,427,027 B2 * | 9/2025 | Ginn | .................. | A61B 17/1757 |
| 2012/0022535 A1 * | 1/2012 | Mayer | .................. | A61F 2/4611 |
| | | | | 606/1 |
| 2012/0296428 A1 * | 11/2012 | Donner | ............. | A61B 17/7043 |
| | | | | 623/17.11 |

(Continued)

FOREIGN PATENT DOCUMENTS

CN          114469455 A  *  5/2022  ......... A61F 2/30734

*Primary Examiner* — Jacqueline T Johanas
(74) *Attorney, Agent, or Firm* — Francis Law Group

(57) ABSTRACT

Prostheses and methods are described for stabilizing dysfunctional sacroiliac (SI) joints. The prostheses are configured to be advanced into dysfunctional SI joints in a posterior trajectory via surgically created pilot SI joint openings in the dysfunctional SI joint. The prostheses have first and second elongated edge sections, and a third elongated section disposed centrally between the first and second elongated sections. The prostheses also have a first bridge sections disposed between and connected to the first and third elongated sections and a second bridge section disposed between and connected to the second and third elongated sections.

11 Claims, 10 Drawing Sheets

(56) References Cited

U.S. PATENT DOCUMENTS

| | | | |
|---|---|---|---|
| 2013/0144343 A1* | 6/2013 | Arnett ................ | A61B 17/7055 |
| | | | 606/279 |
| 2013/0218215 A1* | 8/2013 | Ginn .................. | A61B 17/1604 |
| | | | 606/86 A |
| 2014/0142700 A1* | 5/2014 | Donner .............. | A61B 17/1739 |
| | | | 623/17.11 |
| 2015/0173805 A1* | 6/2015 | Donner .................. | A61B 17/17 |
| | | | 606/279 |
| 2018/0325676 A1* | 11/2018 | Donner .............. | A61B 17/1739 |
| 2023/0000639 A1* | 1/2023 | Stuart ................ | A61B 17/1757 |
| 2024/0335292 A1* | 10/2024 | Boehm, Jr. ........ | A61B 17/1671 |
| 2024/0390151 A1* | 11/2024 | Ginn .................. | A61B 17/7074 |
| 2025/0009396 A1* | 1/2025 | Vestgaarden ...... | A61B 17/7055 |
| 2025/0302632 A1* | 10/2025 | Ginn .................. | A61F 2/30988 |

* cited by examiner

SYSTEMS APPARATUS AND METHODS FOR STABILIZING SACROILIAC JOINTS

CROSS-REFERENCES TO RELATED APPLICATIONS

This application claims the benefit of U.S. Provisional Application No. 63/569,906, filed on Mar. 26, 2024.

FIELD OF THE INVENTION

The present invention relates to systems, apparatus and methods for stabilizing junctions between bone structures. More particularly, the present invention relates to systems, apparatus and methods for stabilizing dysfunctional sacro-iliac (SI) joints.

BACKGROUND OF THE INVENTION

As is well known in the art, the sacroiliac (SI) joint 6 comprises a diarthrodial synovial joint, which, as illustrated in FIG. 1, is defined by the interface between the articular surfaces of the sacrum 2 and the ilium 4. Thus, the SI joint 6 is defined by (and, hence, comprises) portions of the sacrum 2 and ilium 4.

As is also well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3.0°, approximately 1, 5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

Various non-surgical methods, such as administration of pharmacological agents, e.g., the corticosteroid prednisone, and surgical methods and devices, i.e., prostheses, have been developed and employed to treat SI joint dysfunction.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a prosthesis proximate to or in a dysfunctional SI joint and is generally characterized by the direction of access to the dysfunctional SI joint, i.e., anterior, posterior or lateral.

Although several conventional SI joint stabilization surgical methods and associated bone prostheses have effectively ameliorated pain associated with SI joint dysfunction, there remains many disadvantages associated with the conventional methods and associated prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive methods for SI joint stabilization have thus been developed to address the noted disadvantages associated with open surgery methods. Although conventional minimally-invasive SI joint stabilization methods, such as the methods disclosed in U.S. Pub. No. 2009/0076551 to Petersen, have garnered some success in relieving pain associated with SI joint dysfunction and have effectively addressed many of the disadvantages associated with open surgery methods, there similarly remains many disadvantages associated with conventional minimally-invasive SI joint stabilization methods.

A major disadvantage associated with many conventional minimally-invasive SI joint stabilization methods is that such methods are difficult to perform and, hence, often require extensive, system-specific surgical training and experience. Despite the level of surgical training and experience that surgeons possess, when such conventional minimally-invasive SI joint stabilization methods are employed, there is still a substantial incidence of damage to the lumbosacral neurovascular structures proximate to the SI joint.

A further disadvantage associated with many conventional minimally-invasive SI joint stabilization methods and associated apparatus, i.e., prostheses, such as the methods and prostheses disclosed in U.S. Pub. No. 2009/0076551 to Petersen, is that pre-existing sacral abnormalities can lead to displacement of the implanted prostheses, which can, and often will result in damage to surrounding bone and soft tissue structures and, hence, post-procedure pain.

An additional disadvantage associated with many conventional minimally invasive SI joint stabilization methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a prosthesis in a dysfunctional SI joint.

Further, some conventional minimally-invasive SI joint stabilization methods are particularly prone to failure due to displacement of the prostheses in the dysfunctional SI joint and/or failure of the prostheses to effectively engage the SI joint structures, e.g., articular surfaces of the sacrum and/or ilium.

Various "improved" prostheses have thus been developed for use in minimally-invasive SI joint stabilization methods or procedures to effectively engage SI joint structures and maintain engagement thereto during SI joint function.

Although many of the "improved" prostheses, when deployed properly in a dysfunctional SI joint, can, and often will, effectively engage SI joint structures, there remains several disadvantages associated with the prostheses.

A major disadvantage associated with the prostheses designed for minimally-invasive SI joint stabilization are that the noted prostheses are difficult to accurately place in optimum positions in a dysfunctional SI joint and, in many instances, lack sufficient structural properties, such as rigidity and/or fatigue resistance, to effectively stabilize the dysfunctional SI joint.

It would thus be desirable to provide SI joint stabilization systems, apparatus and methods, which substantially reduce or eliminate the disadvantages associated with conventional SI joint stabilization systems, apparatus and methods.

It is therefore an object of the invention to provide improved SI joint stabilization systems, apparatus and methods, which substantially reduce or eliminate the disadvantages associated with conventional SI joint stabilization systems, apparatus and methods.

It is another object of the invention to provide improved minimally-invasive SI joint stabilization systems and apparatus, which can be readily employed to advance prostheses in and, thereby, stabilize dysfunctional SI joints via a posterior trajectory.

It is another object of the invention to provide improved minimally-invasive SI joint stabilization systems and apparatus, which, when implanted in a dysfunctional SI joint, effectively ameliorate pain associated with the SI joint dysfunction.

It is another object of the invention to provide improved SI joint prostheses that can readily be employed in minimally-invasive SI joint stabilization methods and provide secure engagement to SI joint structures.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

4

Figure 2A:
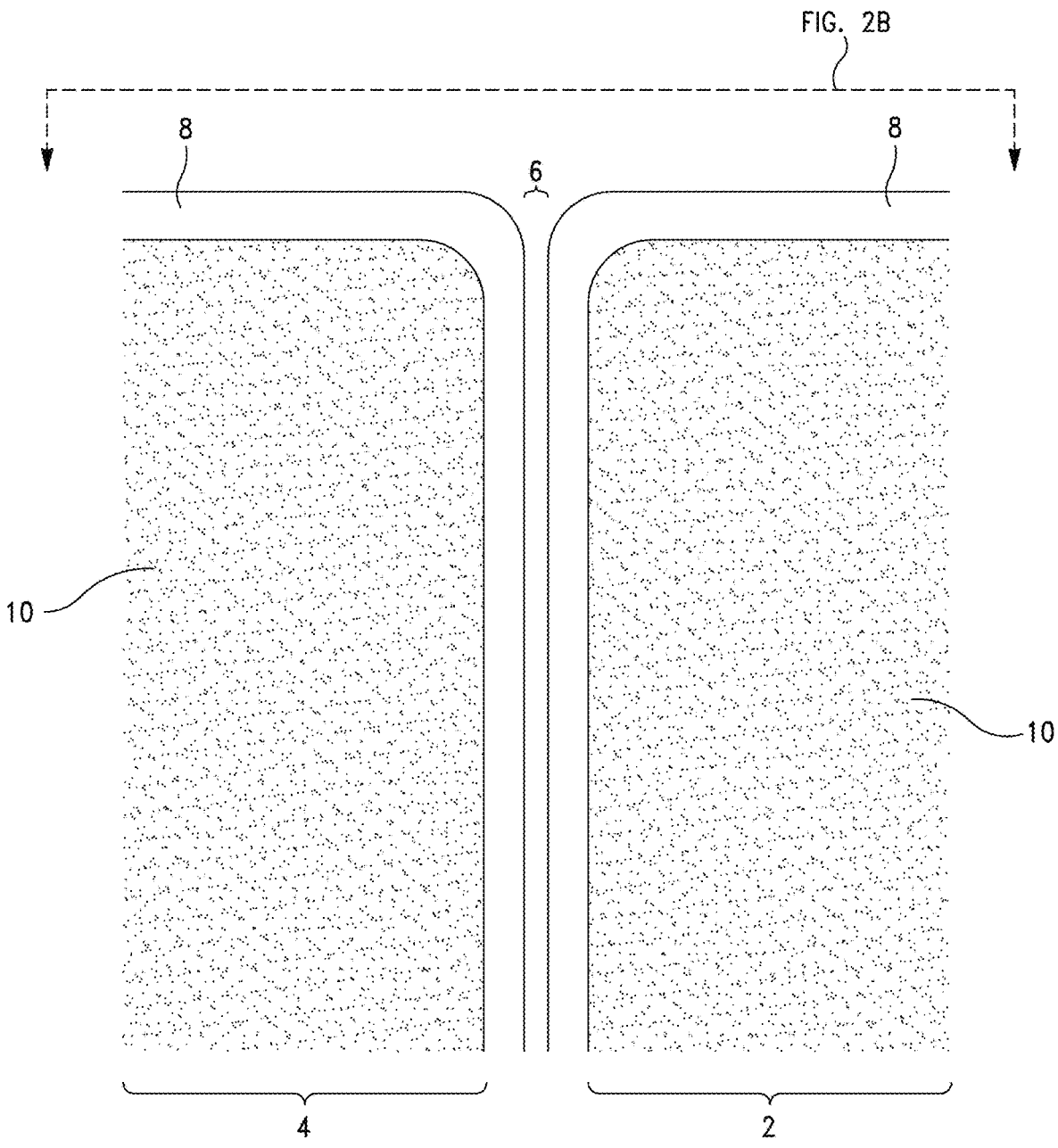
Figure 2B:
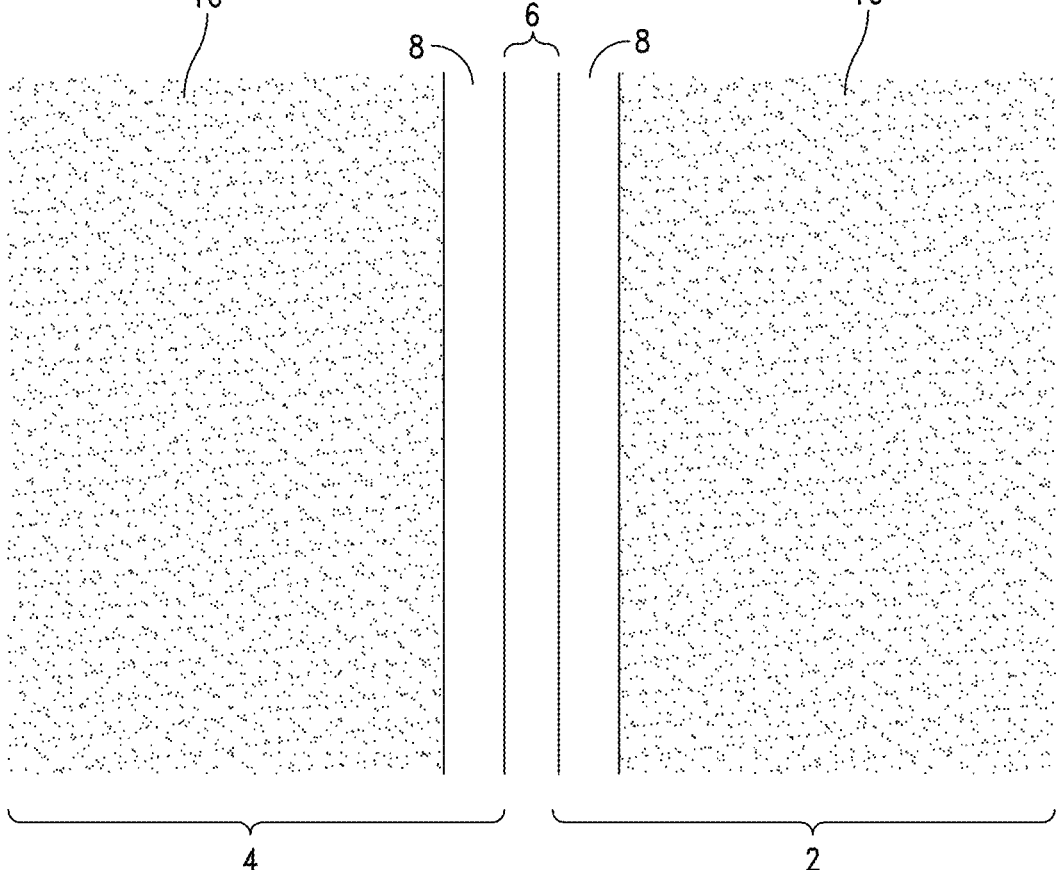
Figure 2C:
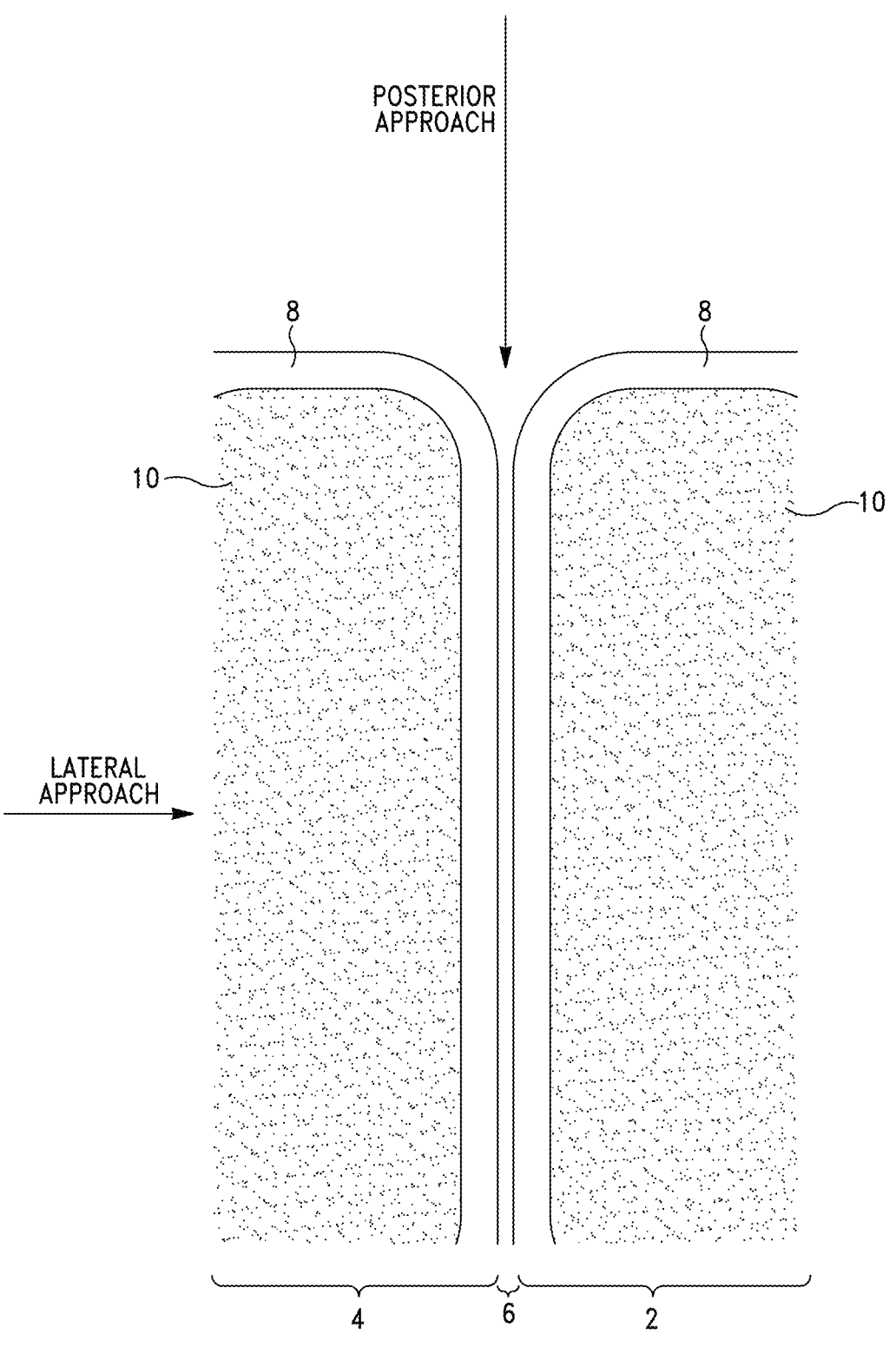
Figure 3A:
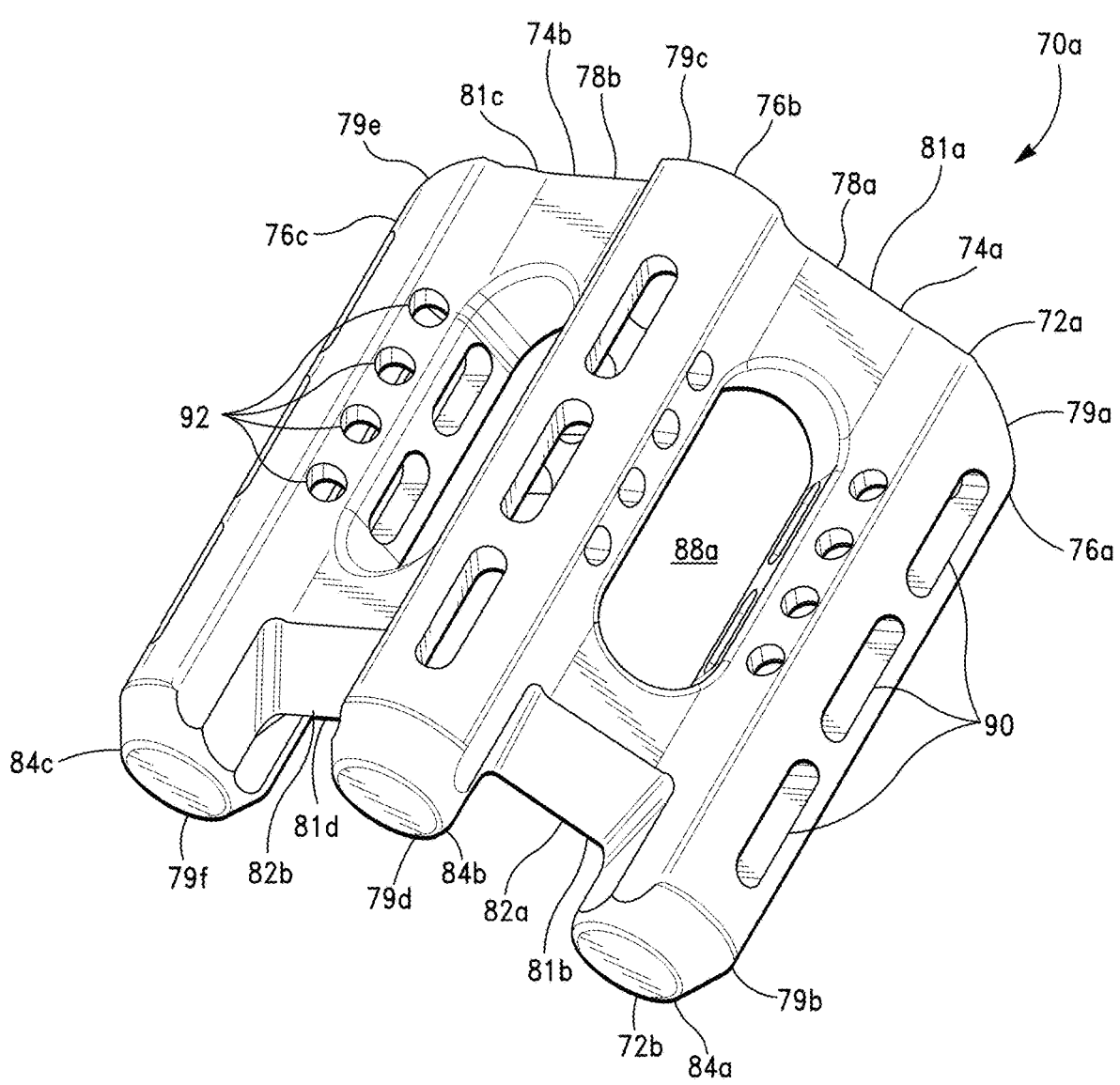
Figure 3B:
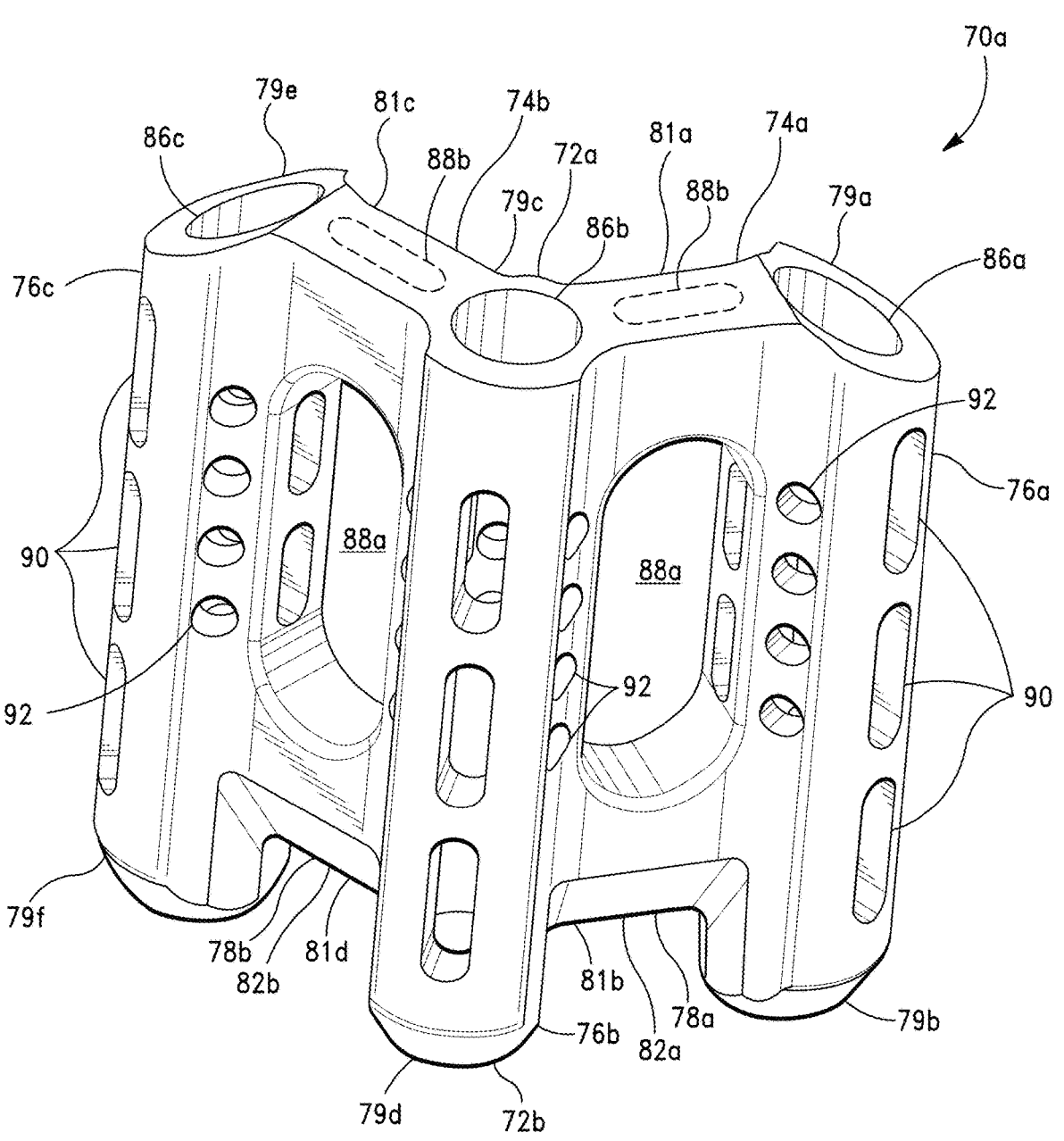
Figure 3C:
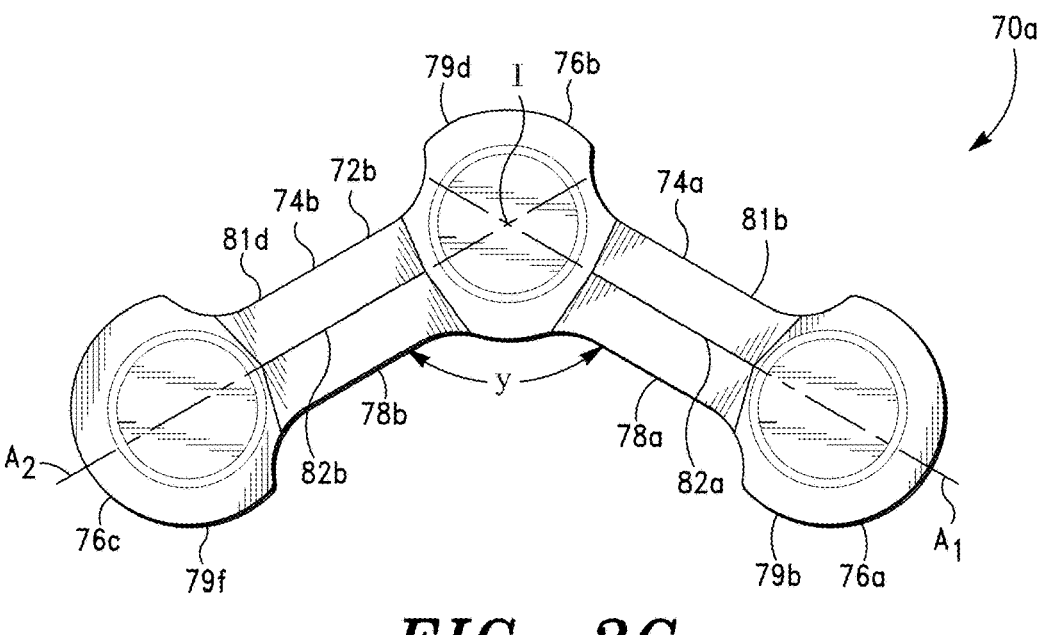
Figure 3D:
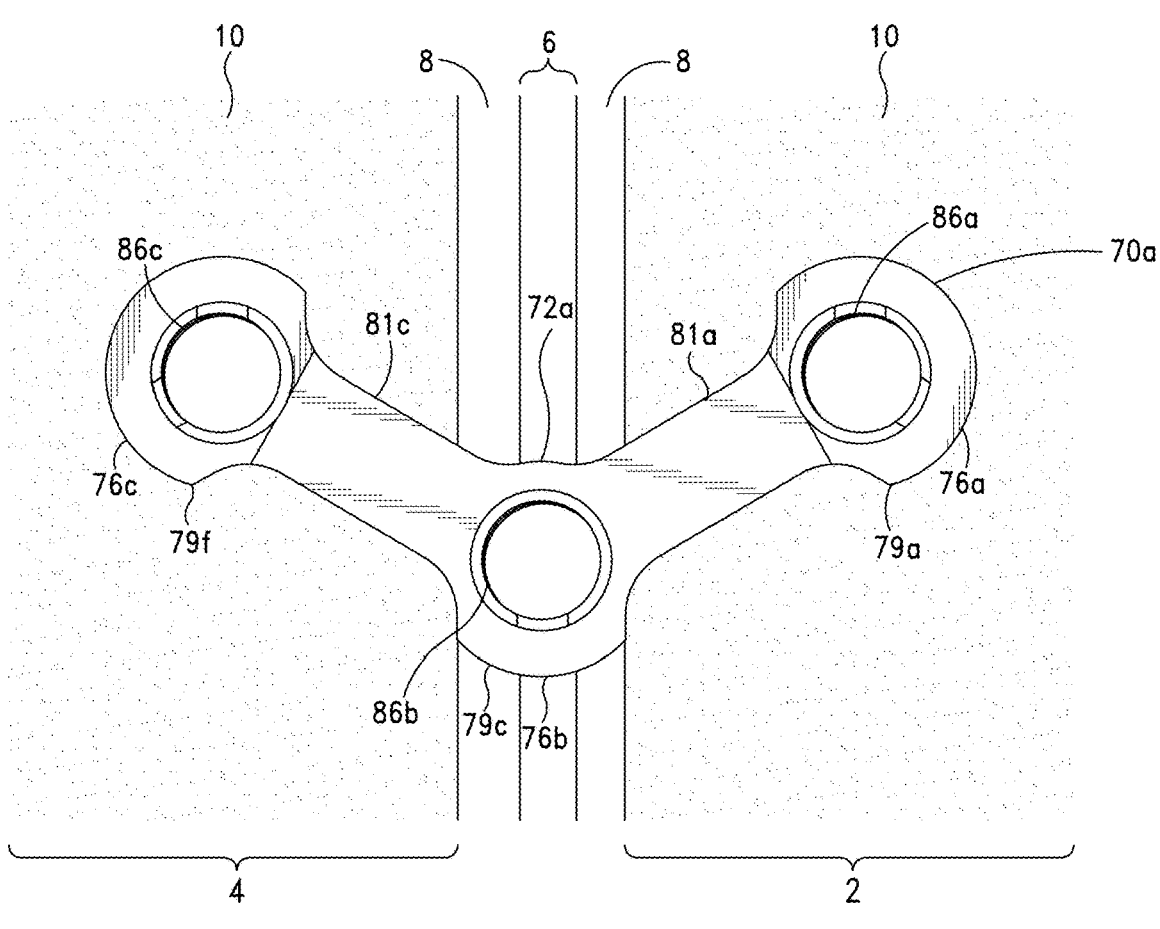
Figure 4A:
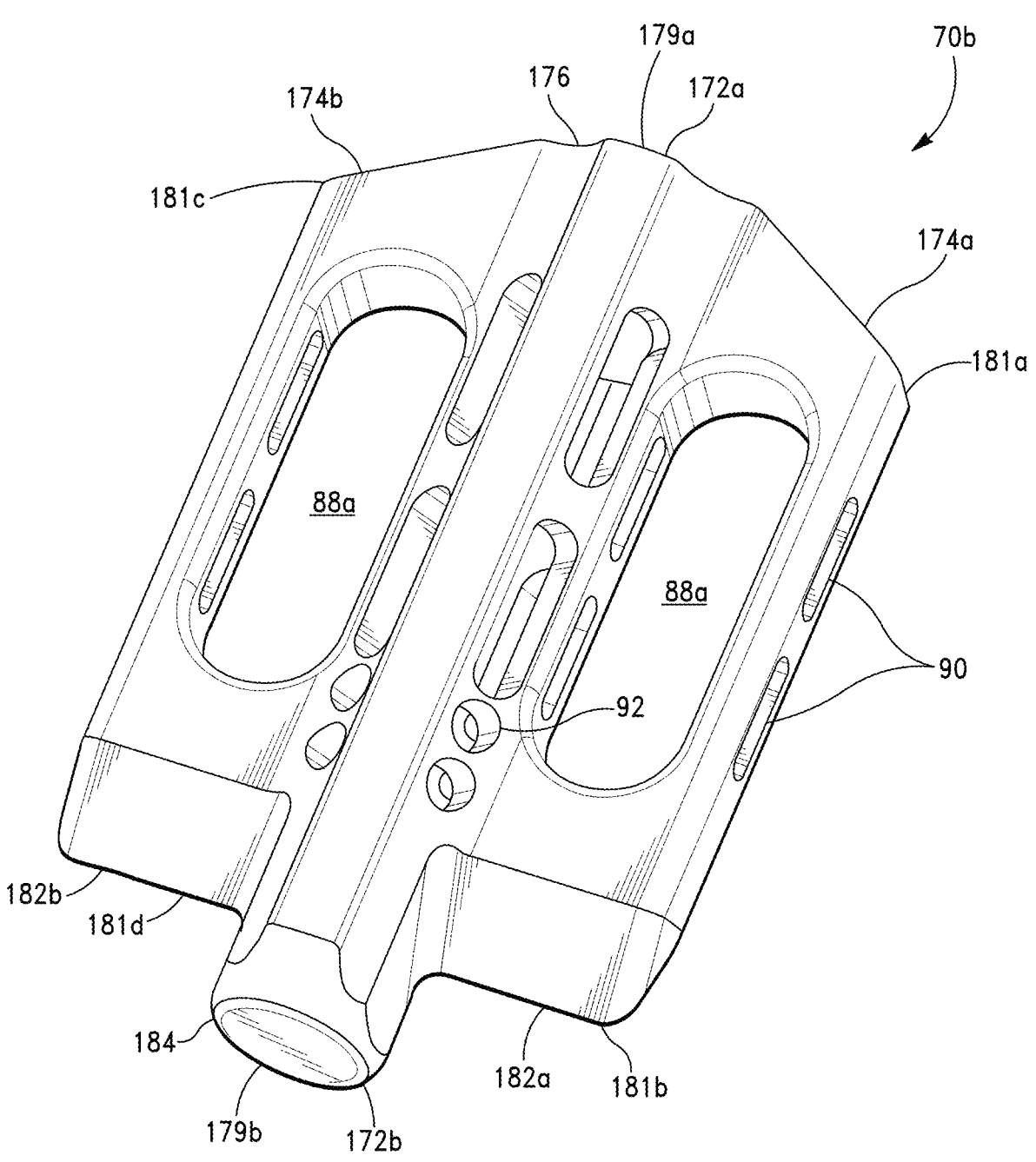
Figure 4B:
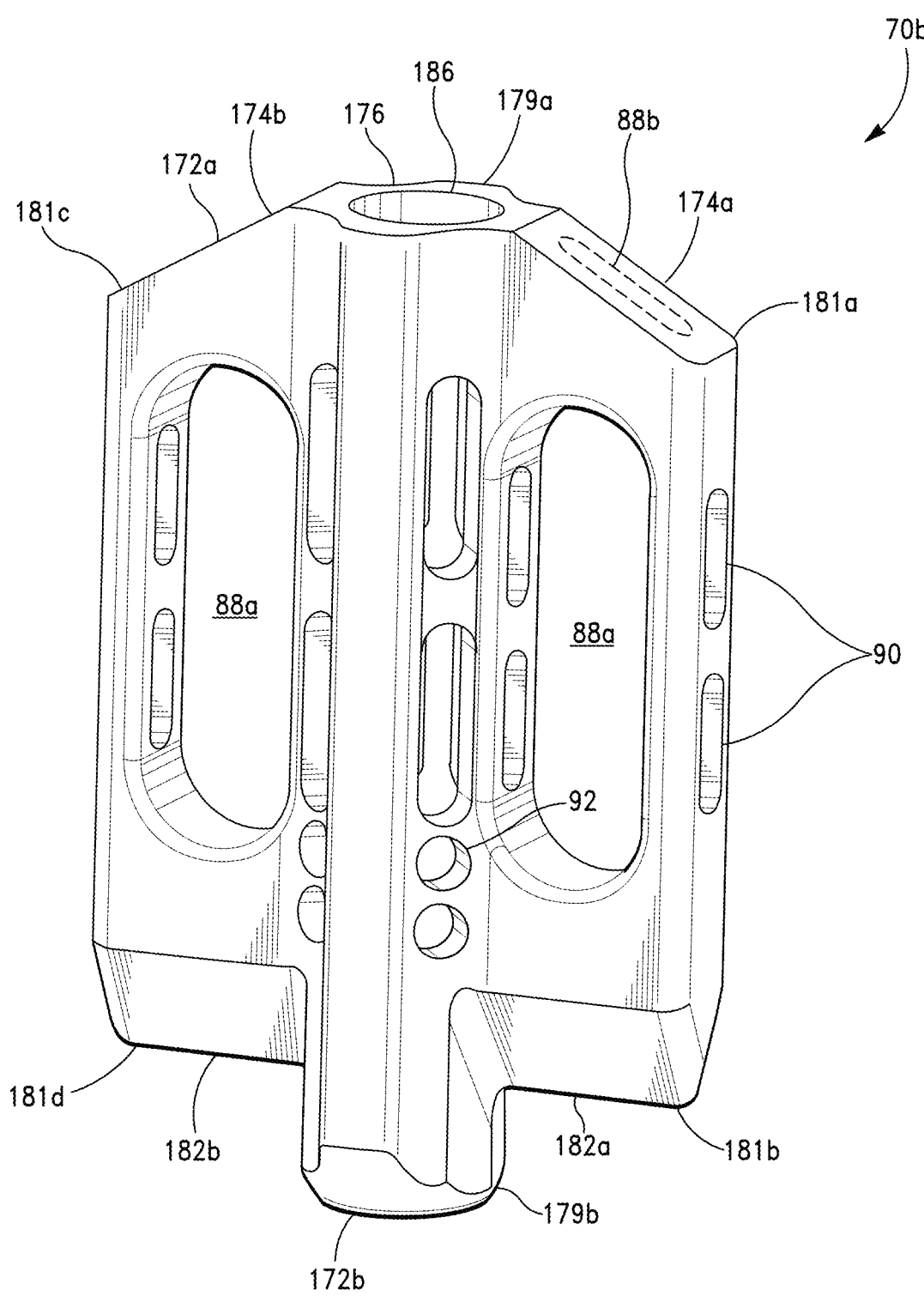
Figure 4C:
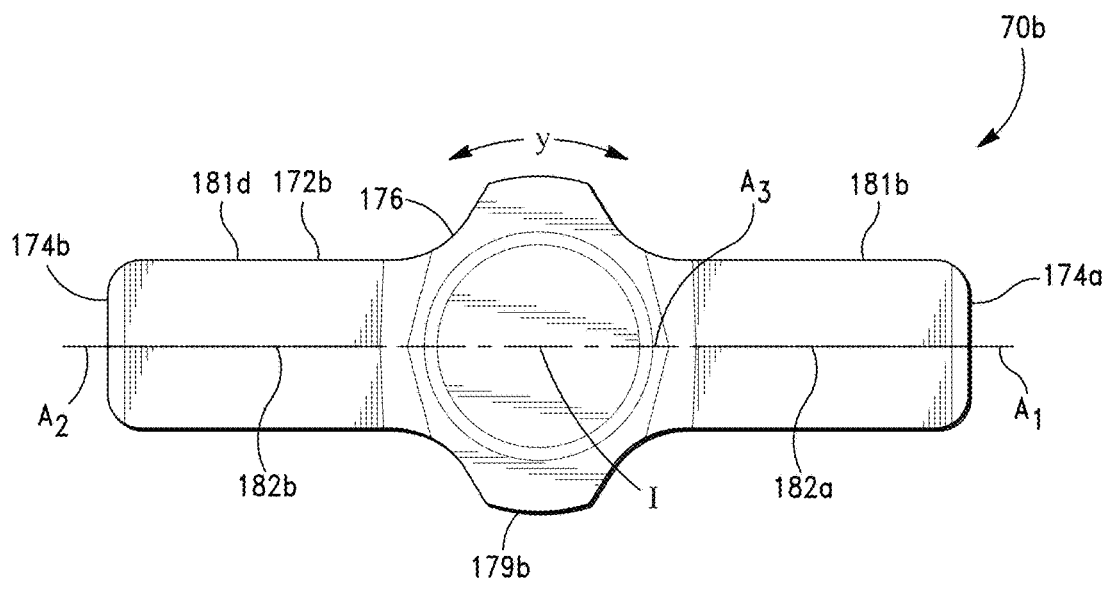
Figure 4D:
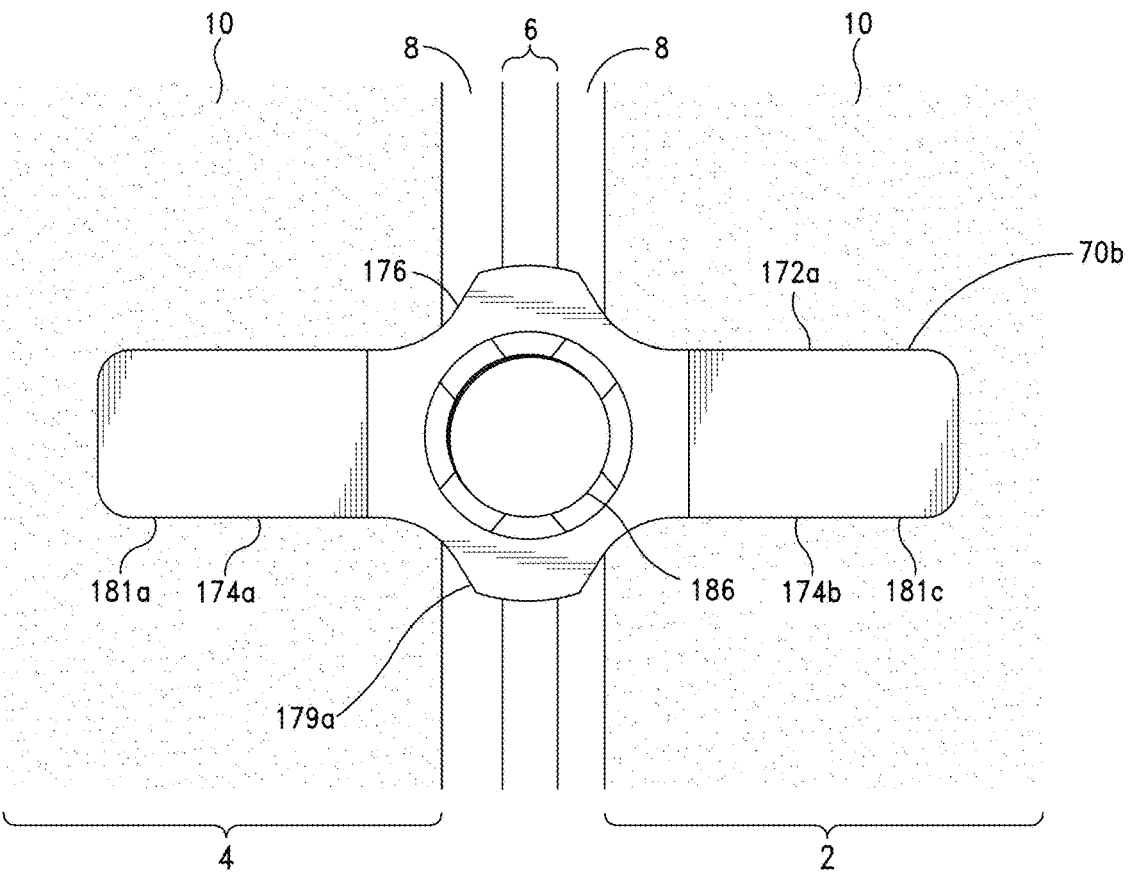

FIG. 2A is an illustration of a SI joint from a superior perspective showing the adjoining sacrum and ilium articular surfaces;

FIG. 2B is another illustration of a SI joint from a posterior perspective showing the adjoining sacrum and ilium articular surfaces;

FIG. 2C is a further illustration of the SI joint shown in FIG. 2A showing lateral and posterior approaches to the SI joint, in accordance with the invention;

FIG. 3A is a top perspective view of one embodiment of a prosthesis, in accordance with the invention;

FIG. 3B is a rear perspective view of the prosthesis shown in FIG. 3A, in accordance with the invention;

FIG. 3C is a front plan view of the prosthesis shown in FIG. 3A, in accordance with the invention;

FIG. 3D is an illustration of the prosthesis shown in FIG. 3A disposed in a SI joint, in accordance with the invention;

FIG. 4A is a top perspective view of another embodiment of a prosthesis, in accordance with the invention;

FIG. 4B is a further top perspective view of the prosthesis shown in FIG. 4A, in accordance with the invention;

FIG. 4C is a front plan view of the prosthesis shown in FIG. 4A, in accordance with the invention; and FIG. 4D is an illustration of the prosthesis shown in FIG. 4A disposed in a SI joint, in accordance with the invention.

DETAILED DESCRIPTION OF THE PREFERRED EMBODIMENT

Before describing the present invention in detail, it is to be understood that this invention is not limited to particularly exemplified apparatus, structures or methods as such may, of course, vary. Thus, although a number of apparatus, structures and methods similar or equivalent to those described herein can be used in the practice of the present invention, the preferred apparatus, systems, structures and methods are described herein.

It is also to be understood that, although the present invention is described and illustrated in connection with sacroiliac (SI) joint stabilization, fixation and fusion procedures, the invention is not limited to such procedures. According to the invention, the apparatus, structures and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a," "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "articular surface" and "articulating surface" are used interchangeably herein in connection with bone structures; particularly, the sacrum and ilium bone structures of a SI joint, and mean and include a surface of a bone structure that forms an articulating junction (i.e., a synovial joint) with an adjacent bone structure, e.g., the articular surfaces of the sacrum and ilium bone structures.

The terms "fusion" and "arthrodesis" are used interchangeably herein in connection with bone structures, and mean and include partial or complete immobilization of adjacent bone structures; particularly, the sacrum and ilium bone structures of a SI joint.

The term "stabilization", as used herein, means and includes reinforcing, e.g., supporting, or modulating motion of adjacent articular bone structures; particularly, the sacrum and ilium bone structures of a SI joint. The term "stabilization", thus, in some instances, means and includes fusion and arthrodesis of adjacent bone structures.

The term "transfix", as used herein in connection with a SI joint, means and includes stabilization of the SI joint via advancement of a prosthesis of the invention into the SI joint and/or the position of the prosthesis after being advanced into the SI joint, wherein the prosthesis intersects (i.e., passes through) the axial and sagittal plans of the ilium and sacrum bone structures of the SI joint, whereby the SI joint is rendered motionless along its longitudinal axis.

The term "prosthesis", as used herein in connection with bone structures, means and includes a system or apparatus configured and adapted to stabilize or modulate motion of articulating bone structures; particularly, the sacrum and ilium bone structures of a SI joint.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly(F-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly($\gamma$-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); poly(ethylene glycol) (PEG) based compositions, including FocalSeal®, Progel™ Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone void filler material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly (F-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)) and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-$\beta$ (TGF-$\beta$), including, TGF-$\beta$1 and TGF-$\beta$2; a growth hormone (GH), parathyroid hormone (PTH, including PTH1-34), transforming growth factor-$\alpha$ (TGF-$\alpha$), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2) and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs) and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-$\alpha$) inhibitors, including etanercept and infliximab, disease-modifying anti-rheumatic drugs (DMARDs), including methotrexate and hydroxychloroquine, antibiotics, anti-viral agents, steroidal anti-inflammatories, non-steroidal anti-inflammatories, anti-thrombotic agents, including anti-coagulants and anti-platelet agents, and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®) and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, mean that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive apparatus and methods for stabilizing dysfunctional SI joints.

In some embodiments of the invention, there are thus provided minimally-invasive apparatus for stabilizing dysfunctional SI joints.

As discussed in detail herein, the apparatus are specifically configured and adapted to be advanced into SI joints in a posterior trajectory, whereby the apparatus transfix the SI joints.

As indicated above, SI joint stabilization, including minimally-invasive SI joint stabilization, typically comprises surgical placement of a prosthesis proximate to or in a dysfunctional SI joint in anterior, lateral and posterior trajectories.

Figure 1:
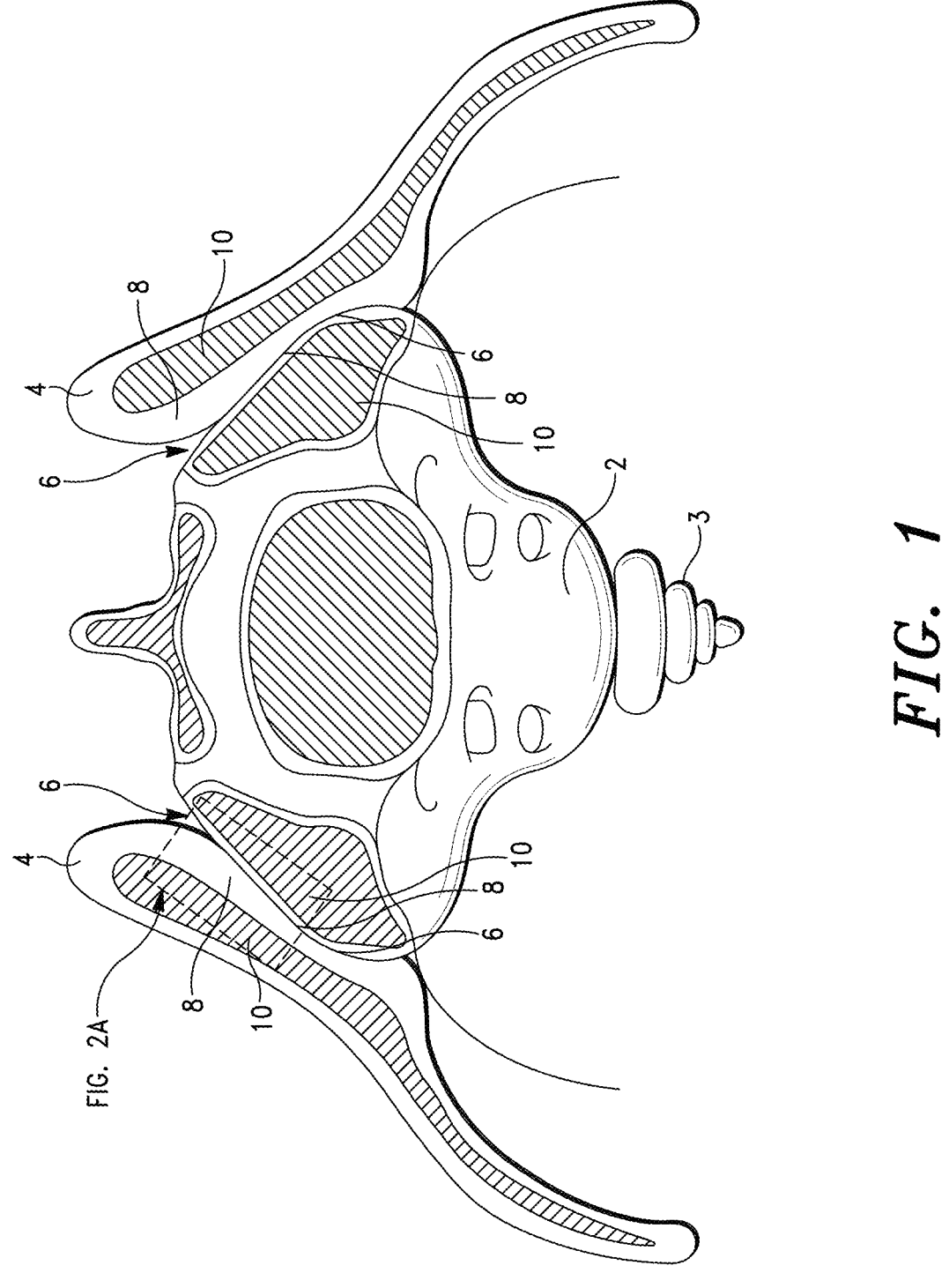
FIG. 1 is a schematic illustration of a human pelvic region from an anteroposterior (AP) perspective showing the SI joints thereof.

From the perspective of FIG. 1, an anterior trajectory to the SI joint 6 (and, hence, a dysfunctional SI joint) would be substantially perpendicular to the page upon which FIG. 1 is printed.

Referring now to FIG. 2A, there is shown a close-up illustration of a portion of the leftmost SI joint 6 illustrated in FIG. 1. For illustrative simplicity, a uniform layer of cortical bone 8 is shown adjacent to a deeper layer of trabecular bone 10 on both of the depicted sacrum 2 and ilium 4 portions. However, in actuality, such layers are far less uniform and homogeneous.

Referring now to FIG. 2B, there is shown a view of the same structure from a different posterior perspective. From the perspective of FIG. 2B, a posterior trajectory to the SI joint 6 (and, hence, a dysfunctional SI joint) would be substantially perpendicular to the page upon which FIG. 2B is printed. Indeed, referring to FIG. 2C, a variation similar to that depicted in FIG. 2A is illustrated, showing an approximate approach vector for a lateral trajectory to the SI joint 6 versus a posterior trajectory, using the orientation paradigms introduced in FIGS. 1 and 2A-2C. Such paradigms are used to illustrate various embodiments of the subject invention in various figures that follow FIGS. 1 and 2A-2C.

As indicated above, a major disadvantage associated with many conventional anterior or lateral trajectories to a dysfunctional SI joint is that muscles and ligaments are typically disrupted and often damaged. Nerves and blood vessels are also susceptible to damage during such SI joint stabilization methods.

In contrast, a posterior trajectory to a dysfunctional SI joint is much less invasive. Indeed, less tissue and fewer muscles are disrupted, and nerves and large blood vessels are avoided.

Thus, in a preferred embodiment, the prostheses of the invention are configured and adapted to provide minimally-invasive stabilization of a dysfunctional SI joint via advancement of the prostheses into the dysfunctional SI joint in a posterior trajectory.

Referring now to FIGS. 3A-3C, there is shown one embodiment of a prosthesis of the invention (denoted "70a").

In a preferred embodiment, prosthesis 70a is configured and adapted to be advanced into a dysfunctional SI joint in a posterior trajectory, such as illustrated in FIG. 3D, wherein the prosthesis transfixes the SI joint.

As illustrated in FIGS. 3A and 3B, in a preferred embodiment, the prosthesis 70a comprises an elongated implantable member comprising proximal and distal ends 72a, 72b, and first, second and third interconnected elongated sections 76a, 76b, 76c.

As further illustrated in FIGS. 3A and 3B, in a preferred embodiment, the elongated sections 76a, 76b are connected to bridge section 78a, and the elongated sections 76c and 76b are connected to bridge section 78b, wherein the prosthesis 70a comprises first and second arms (or members) 74a, 74b.

As illustrated in FIG. 3C, the first arm 74a of prosthesis 70a comprises a first longitudinal axis $A_1$ and the second arm 74b comprises a second longitudinal axis $A_2$, which intersect at point "I" (i.e., center of elongated section 76b) and form structure angle "7". In a preferred embodiment, the structure angle "$\gamma$" is in the range of approximately 3.0° to 350.0°, more preferably, 10.0° to 180.0°, even more preferably, 20.0° to 160.0°.

Thus, in some embodiments, the structure angle "$\gamma$" is <180.0°, wherein the second elongated section 76b is offset from first and third elongated sections 76a and 76c and the prosthesis 70a comprises a V-shaped structure, as illustrated in FIG. 3C.

In some embodiments, the structure angle "$\gamma$" is approximately equal to 180.0°, wherein the first, second and third elongated section 76a, 76b, 76c are disposed on a common linear plane.

Referring back to FIGS. 3A and 3B, the first elongated section 76a comprises proximal and distal ends 79a, 79b, the second elongated section 76b comprises proximal and distal ends 79c, 79d, and the third elongated section 76c comprises proximal and distal ends 79e, 79f.

As further illustrated in FIGS. 3A and 3B, the bridge section 78a comprises proximal and distal ends 81a, 81b, and the bridge section 78b comprises proximal and distal ends 81c, 81d.

According to the invention, the prosthesis 70a can comprise any suitable length from the proximal end 72a to the distal end 72b thereof. In some embodiments, the prosthesis 70a comprises a length in the range of 20.0-50.0 mm. In a preferred embodiment, the prosthesis 70a comprises a length in the range of 30.0-40.0 mm.

According to the invention, the first and third elongated sections 76a, 76c of the prosthesis 70a can comprise the same length or different lengths, e.g., the first elongated section 76a comprises a greater length than the third elongated section 76c.

According to the invention, the length of the second elongated section 76b can also be greater or less than the length of the first and third elongated sections 76a, 76c of the prosthesis 70a.

As illustrated in FIG. 3A, in a preferred embodiment, the distal ends 79b, 79d, 79f of the first, second and third elongated sections 76a, 76b, 76c comprise tapered regions 84a, 84b, 84c, which are configured to facilitate insertion of the first, second and third elongated sections 76a, 76b, 76c into pilot openings in a SI joint.

As illustrated in FIG. 3B, the first elongated section 76a of prosthesis 70a comprises a first prosthesis lumen 86a that extends from the proximal end 79a of the first elongated section 76a, the second elongated section 76b comprises a second prosthesis lumen 86b that extends from the proximal end 79c of the second elongated section 76b, and the third elongated section 76c comprises a third prosthesis lumen 86c that extends from the proximal end 79e of the second elongated section 76c.

In a preferred embodiment, at least the first and third prosthesis lumens 86a, 86c of prosthesis 70a are sized and configured to receive the prosthesis engagement rods of the prosthesis deployment assembly and/or prosthesis extraction screws of the prosthesis extraction assembly described in Applicant's Co-pending U.S. application Ser. No. 17/899, 693, which is incorporated by reference herein in its entirety.

In some embodiments, the first and third prosthesis lumens 86a, 86c of prosthesis 70a thus comprise a threaded region proximate the proximal ends 79a, 79e of elongated sections 76a, 76c, which is sized and configured to receive and threadably engage the prosthesis engagement rods of the prosthesis deployment assembly and the prosthesis extraction screws of the prosthesis extraction assembly.

In a preferred embodiment, the prosthesis lumens 86a, 86b, 86c are configured to receive agents and compositions that facilitate adhesion of the prosthesis 70a to a SI joint and the biologically active agents and compositions referenced above, including osteogenic agents and compositions, and pharmacological agents and compositions that facilitate osseous or bone tissue ingrowth into the prosthesis 70a and healing of SI joint bone structures.

As further illustrated in FIGS. 3A and 3B, in a preferred embodiment, the elongated sections 76a, 76b, 76c of prosthesis 70a further comprise a plurality of slots 90 and holes 92, which preferably are in communication with prosthesis lumens 86a, 86b, 86c.

In a preferred embodiment, the slots 90 and holes 92 of prosthesis 70a are sized and configured to receive the aforementioned agents and compositions and disperse the agents and compositions into a SI joint when the prosthesis 70a is advanced into the SI joint.

As further illustrated in FIG. 3A, in a preferred embodiment, the distal ends 81b, 81d of bridge sections 78a, 78b comprise taper regions 82a, 82b, which are configured and adapted to disrupt, i.e., cut into and through, at least articular cartilage and cortical bone, when the prosthesis 70a is advanced into a SI joint.

As further illustrated in FIGS. 3A and 3B, the bridge sections 78a, 78b further comprise central open regions 88a, which are preferably in communication with slots 90.

According to the invention, the bridge sections 78a, 78b can also comprise proximal bridge openings (shown in phantom and denoted "88b" in FIG. 3B), which extend from the proximal ends 81a, 81c of the bridge sections 78a, 78b to the central openings 88a of the bridge sections 78a, 78b. According to the invention, the proximal bridge openings 88b can comprise any suitable size and/or configuration.

Referring now to FIGS. 4A-4C, there is shown another embodiment of a prosthesis of the invention (denoted "70b") comprising proximal and distal ends 172a, 172b.

In a preferred embodiment, prosthesis 70b is similarly configured and adapted to be advanced into a dysfunctional SI joint in a posterior trajectory, such as illustrated in FIG. 4D, wherein the prosthesis 70b transfixes the dysfunctional SI joint.

As illustrated in FIGS. 4A and 4B, in a preferred embodiment, the prosthesis 70b similarly comprises an elongated implantable member comprising an elongated section 176 and first and second arms (or wings) 174a, 174b, the elongated section 176 being disposed between and connected to the first and second arms 174a, 174b.

As illustrated in FIG. 4C, the first arm 174a of prosthesis 70b similarly comprises first longitudinal axis $A_1$ and the second arm 174b similarly comprises second longitudinal axis $A_2$, which intersect at point "I" (i.e., center of elongated section 176).

According to the invention, the first and second longitudinal axes $A_1$, $A_2$ similarly form structure angle "$\gamma$" at intersect point "I".

According to the invention, the structure angle "$\gamma$" of prosthesis 70b can similarly be in the range of approximately 3.00 to 350.0°.

Thus, in some embodiments, the structure angle "$\gamma$" of prosthesis 70b is in the range of approximately 10.0° to 180.0°.

In a preferred embodiment, the structure angle "$\gamma$" of prosthesis 70b is approximately 180.0°, whereby the first and second longitudinal axes $A_1$, $A_2$ form a common longitudinal axis $A_3$, as illustrated in FIG. 4C.

Referring back to FIGS. 4A and 4B, the elongated section 176 of prosthesis 70b comprises proximal and distal ends 179a, 179b, the first arm 174a comprises proximal and distal ends 181a, 181b, and the second arm 174b comprises proximal and distal ends 181c, 181d.

According to the invention, the prosthesis 70b can similarly comprise any suitable length from the proximal end 179a to the distal end 179b of elongated section 176. In some embodiments, the prosthesis 70b comprises a length in the range of 20.0-50.0 mm. In a preferred embodiment, the prosthesis 70b similarly comprises a length in the range of 30.0-40.0 mm.

According to the invention, the length of the elongated section 176 can be the same, less than or greater than the length of the first and second arms 174a, 174b.

As illustrated in FIGS. 4A and 4B, in a preferred embodiment, the length of the elongated section 176 is greater than the length(s) of the first and second arms 174a, 174b.

As illustrated in FIG. 4A, in a preferred embodiment, the distal end 179b of elongated section 176 comprises a tapered region 184, which is similarly configured to facilitate insertion of elongated section 176 into a pilot opening in a SI joint.

As illustrated in FIG. 4B, the elongated section 176 of prosthesis 70b further comprises a prosthesis lumen 186 that extends from the proximal end 179a of elongated section 176. In some embodiments, the prosthesis lumen 186 comprises a threaded region proximate the proximal end 179a of the elongated section 176.

In a preferred embodiment, the prosthesis lumen 186 is similarly configured to receive agents and compositions that facilitate adhesion of the prosthesis 70b to a SI joint and the biologically active agents and compositions referenced above, including osteogenic agents and compositions, and pharmacological agents and compositions that facilitate osseous or bone tissue ingrowth into the prosthesis 70b and healing of SI joint bone structures.

As further illustrated in FIGS. 4A and 4B, in a preferred embodiment, the elongated section 176 of prosthesis 70b further comprises a plurality of slots 90 and holes 92, which preferably are in communication with prosthesis lumen 186. In a preferred embodiment, the first and second arms 174a, 174b of prosthesis 70b also comprise a plurality of slots 90.

In a preferred embodiment, the slots 90 and holes 92 of prosthesis 70b are similarly sized and configured to receive the aforementioned agents and compositions and disperse the agents and compositions into a SI joint when the prosthesis 70b is advanced into the SI joint.

As further illustrated in FIG. 4A, in a preferred embodiment, the distal ends 181b, 181d of prosthesis arms 174a, 174b comprise taper regions 182a, 182b, which are similarly configured and adapted to disrupt, i.e., cut into and through, at least articular cartilage and cortical bone, when the prosthesis 70b is advanced into a SI joint.

As further illustrated in FIGS. 4A and 4B, the prosthesis arms 174a, 174b further comprise central open regions 88a.

According to the invention, the prosthesis arms 174a, 174b can also comprise proximal arm openings (shown in phantom and denoted "88b" in FIG. 4B), which extend from the proximal ends 181a, 181c of the prosthesis arms 174a, 174b to the central openings 88a of the arms 174a, 174b.

As indicated above, the prostheses 70a and 70b, discussed above, are specifically adapted to be advanced into SI joints; particularly, dysfunctional SI joints, in a posterior trajectory, wherein the prostheses transfix the SI joints.

According to the invention, the prostheses 70a and 70b can comprise various biocompatible materials, including metals and metal alloys, such as titanium, stainless-steel, cobalt-chromium alloys, and nickel-titanium alloys.

Prostheses 70a and 70b can also comprise various biocompatible polymers, including, without limitation, reinforced polymers, such as carbon fiber reinforced polymers and metal-framed polymers.

According to the invention, prostheses 70a and 70b can also comprise various exterior surface textures and roughness to facilitate or enhance engagement of the prostheses to post-prosthesis insertion SI joint openings formed by the prostheses 70a and 70b and, thereby, to SI joint bone structures, i.e., sacrum and ilium bone structures, and/or maintain engagement thereto and positioning therein.

The surface of the prostheses can, thus, comprise a roughness grade number of N1 (Ra=~0.025 μm), N2 (Ra=~0.05 μm), N3 (Ra=~0.1 μm), N4 (Ra=~0.2 μm), N5 (Ra=~0.4 μm), N6 (Ra=~0.08 μm), N7 (Ra=~1.6 μm), N8 (Ra=~3.2 μm), N9 (Ra=~6.3 μm), N10 (Ra=~12.5 μm), N11 (Ra=~25 μm) or N12 (Ra=~50 μm).

In some embodiments of the invention, prostheses 70a and 70b can further comprise an outer coating.

In some embodiments, the outer coating comprises a biocompatible and, preferably, biodegradable adhesive composition. According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and Octyl-Seal); poly(ethylene glycol) (PEG) based compositions, including FocalSeal®, Progel™ Duraseal™, DuraSeal™ Xact, Coseal® and ReSure Sealant; polysaccharide-based compositions, polypeptide-based compositions, and radiation curable materials, such as poly(glycerol-co-sebacate) acrylate (PGSA), discussed below.

In some embodiments, the outer coating comprises a biologically active composition comprising one of the aforementioned biologically active agents (referred to generally as fixation catalysts in application Ser. No. 13/857,977, now U.S. Pat. No. 11,273,042) or a pharmacological composition comprising one of the forementioned pharmacological agents.

In some embodiments, the outer coating comprises one of the aforementioned polymers and/or compositions comprising same.

In some embodiments, the aforementioned polymer compositions comprise one or more of the aforementioned biologically active agents or pharmacological agents.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite 15                                                                                      16

(HA) composites and PGS-poly(F-caprolactone) (PGS-PCL) composites, and compositions comprising same.

As set forth in Co-pending U.S. application Ser. No. 17/463,779, PGS and derivatives thereof possess a unique property of inducing remodeling of damaged osseous or bone tissue, such as at pilot SI joint openings, and, hence, healing of the associated bone structures when disposed proximate thereto.

As set forth in Loh, et al., *Poly(glycerol sebacate) Biomaterial: Synthesis and Biomedical Applications*, Journal of Materials Chemistry B, vol. 3(39), pp. 7641-7652 (2015) and indicated in Table 1 below, a further seminal property of PGS is that its physical state can be modulated during synthesis by controlling the "degree of esterification" via at least one crosslinking agent, e.g., methylene diphenyl diisocyanate (MDI).

TABLE 1

| Degree of Esterification | Physical State |
| --- | --- |
| ≤46% | Solid (Brittle Wax) |
| ~47%-64% | Semi-Solid (Soft Wax) |
| ~65%-75% | Viscous Liquid |
| ~76%-83% | Sticky Elastomer |
| ≥84% | Elastomer |

According to the invention, any suitable degree of esterification of PGS can be employed for PGS when employed in or for PGS based outer coatings (i.e., polymer compositions comprising PGS) and biologically active agent compositions of the invention.

In some embodiments, the PGS based outer coatings comprise a degree of esterification in the range of ~76%-83%, whereby the PGS exhibits adhesive properties, which will enhance engagement of the prostheses of the invention; particularly prostheses 70a and 70b, to post-prosthesis insertion SI joint openings created by the prostheses 70a and 70b and, thereby, to the SI joint bone structures, i.e., sacrum and ilium bone structures.

As is well established, the physical state of poly(glycerol-co-sebacate) acrylate (PGSA) can also be modulated by combining the PGSA with a suitable photoinitiator and subjecting the PGSA to radiation.

Indeed, as set forth in Nijst, et al., *Synthesis and Characterization of Photocurable Elastomers from Poly(Glycerol-Co-Sebacate)*, Biomacromolecules, vol. 8, no. 10, pp. 3067-3073 (2007), PGSA can be induced to transition from a liquid or flowable state to a solid elastomer state when combined with a photoinitiator, such as 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl and methylcyclopentadienyl manganese tricarbonyl, and subjected to radiation, such as visible light; particularly, radiation in the range of approximately 380.0 nm-750.0 nm, and ultraviolet (UV) light, particularly, radiation in the range of 10.0 nm-400.0 nm.

Thus, in some embodiments, a composition comprising PGSA (also referred to herein as a "PGSA based composition" and "fixation composition") is employed to enhance the engagement of prostheses 70a and 70b to SI joint bone structures, i.e., sacrum and ilium bone structures.

In some embodiments, the PGSA based composition (in a flowable state) is thus disposed in prosthesis lumens 86a, 86b, 86c of prosthesis 70a, and prosthesis lumen 186 of prosthesis 70b, whereby the PGSA based composition is dispersed when the prostheses 70a and 70b are advanced into a SI joint and fills any gaps between the prostheses 70a and 70b and pilot openings in the SI joint, and is thereafter cured via radiation and solidified, whereby the solidified PGSA enhances the engagement of the prostheses 70a and 70b to the SI joint.

PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS based outer coatings and PGS and PGSA based compositions further comprise one or more of the aforementioned biologically active or pharmacological agents.

Without departing from the spirit and scope of this invention, one of ordinary skill can make various changes and modifications to the invention to adapt it to various usages and conditions.

What is claimed is:

1. An apparatus for stabilizing a dysfunctional sacroiliac (SI) joint, said dysfunctional SI joint comprising a sacrum bone structure, an ilium bone structure and an intraarticular region disposed between said sacrum bone structure and said ilium bone structure, said apparatus comprising:

a monolithic member configured and adapted to be advanced into said dysfunctional SI joint in a posterior trajectory, wherein said monolithic member transfixes said dysfunctional SI joint, said monolithic member comprising a first elongated section, a second elongated section and a third elongated section disposed between said first elongated section and said second elongated section, said monolithic member further comprising a first bridge section and a second bridge section, said first bridge section disposed between and connected to said first elongated section and said third elongated section, said second bridge section disposed between and connected to said second elongated section and said third elongated section, said first elongated section configured to be advanced into said sacrum bone structure when said monolithic member is said advanced into said dysfunctional SI joint in said posterior trajectory, said first elongated section comprising a first central longitudinal axis, a first open proximal end and a first closed distal end, said second elongated section configured to be advanced into said ilium bone structure of said dysfunctional SI joint when said monolithic member is said advanced into said dysfunctional SI joint in said posterior trajectory, said second elongated section comprising a second central longitudinal axis, a second open proximal end and a second closed distal end, said first elongated section and said second elongated section defining a monolithic member plane that intersects and is coincident with said first central longitudinal axis of said first elongated section and said second central longitudinal axis of said second elongated section, said third elongated section configured to be advanced into said intraarticular region of said dysfunctional SI joint when said first elongated section is said advanced into said sacrum bone structure and said second elongated section is said advanced into said ilium bone structure of said dysfunctional SI joint, said third elongated section comprising a third open proximal end and a third closed distal end, said third elongated section being offset from said first elongated section and said second elongated section in a first vertical direction, whereby said third elongated section extends beyond said first elongated section and said second elongated section in said first vertical direction.

2. The apparatus of claim 1, wherein said first closed distal end of said first elongated section comprises a first tapered region, and said second closed distal end of said second elongated section comprises a second tapered region.

3. The apparatus of claim 1, wherein said third closed distal end of said third elongated section comprises a third tapered region.

4. The apparatus of claim 1, wherein said first bridge section comprises a first proximal end, a first distal end and a first elongate opening disposed between said first proximal end of said first bridge section and said first distal end of said first bridge section and extending through said first bridge section.

5. The apparatus of claim 4, wherein said second bridge section comprises a second proximal end, a second distal end and a second elongate opening disposed between said second proximal end of said second bridge section and said second distal end of said second bridge section and extending through said second bridge section.

6. The apparatus of claim 1, wherein said first elongated section of said monolithic member further comprises a first plurality of slots.

7. The apparatus of claim 6, wherein said first elongated section of said monolithic member further comprises a first internal lumen in communication with said first open proximal end and said first plurality of slots of said first elongated section, said first internal lumen adapted to receive a first osteogenic composition therein.

8. The apparatus of claim 1, wherein said second elongated section of said monolithic member further comprises a second plurality of slots.

9. The apparatus of claim 8, wherein said second elongated section of said monolithic member further comprises a second internal lumen in communication with said second open proximal end and said second plurality of slots of said second elongated section, said second internal lumen adapted to receive a second osteogenic composition therein.

10. The apparatus of claim 1, wherein said third elongated section of said monolithic member further comprises a third plurality of slots.

11. The apparatus of claim 10, wherein said third elongated section of said monolithic member further comprises a third internal lumen in communication with said third open proximal end and said third plurality of slots of said third elongated section, said third internal lumen adapted to receive a third osteogenic composition therein.

\* \* \* \* \*